United States Patent [19]

Bruzzese

[11] Patent Number: 5,776,978

[45] Date of Patent: Jul. 7, 1998

[54] PHARMACEUTICAL PREPARATIONS CONTAINING POLYUNSATURATED FATTY ACIDS, THEIR ESTERS OR SALTS, TOGETHER WITH ANTIOXIDANT VITAMINS OR PROVITAMINS

[75] Inventor: Tiberio Bruzzese, Milano, Italy

[73] Assignee: Prospa B.V., Amsterdam, Netherlands

[21] Appl. No.: 517,900

[22] Filed: Aug. 22, 1995

[30] Foreign Application Priority Data

Aug. 25, 1994 [IT] Italy ................... MI94A1774

[51] Int. Cl.$^6$ ................... A61K 31/355; A61K 31/20
[52] U.S. Cl. ................... 514/558; 514/458
[58] Field of Search ................... 514/558, 560, 514/549, 578, 458

[56] References Cited

U.S. PATENT DOCUMENTS 5,415,879  5/1995  Oh ................... 426/2
5,502,077  3/1996  Breivik et al. ................... 514/560

Primary Examiner—Theodore J. Criares
Attorney, Agent, or Firm—Griffin, Butler Whisenhunt & Kurtossy

[57] ABSTRACT

Pharmaceutical preparations are described, useful in the prevention and/or treatment of atherosclerosis, of cardiovascular, nervous system, skin and malignant pathologies, containing 50 to 1000 mg of omega-3 fatty acids, their esters and their salts with inorganic and organic bases, as individual compounds or as a mixture, in combination with 10–40% by weight of antioxidant/reducing vitamins or provitamins.

7 Claims, No Drawings

PHARMACEUTICAL PREPARATIONS CONTAINING POLYUNSATURATED FATTY ACIDS, THEIR ESTERS OR SALTS, TOGETHER WITH ANTIOXIDANT VITAMINS OR PROVITAMINS

Pharmaceutical preparations are described, useful in the prevention and/or treatment of atherosclerosis, of cardiovascular, nervous system, skin and malignant pathologies, containing 50 to 1000 mg of omega-3 fatty acids, their esters and their salts with inorganic and organic bases, as individual compounds or as a mixture, in combination with 10–40% by weight of antioxidant/reducing vitamins or provitamins.

The present invention refers to pharmaceutical preparations containing omega-3 polyunsaturated fatty acids and suitable quantities of vitamins or provitamins having reducing or antioxidant activity, to be used in the treatment of atherosclerosis or of other pathologies both of the cardiovascular or not cardiovascular type, such as, in example, diseases of the central nervous system, of the skin, inflammatory or neoplastic conditions, etc. The combined use of omega-3 polyunsaturated fatty acids and of highly fatsoluble vitamins, as subsequently described, next to the above mentioned pharmacologic and therapeutic action which will be discussed in due time, also leads to reciprocal potentiation of the respective fat-solubility, and, in the end, to better availability of their combination as compared to the individual constituents. 4,7,10,13,16,19-cis docosahexaenoic acid (hereinafter called DHA) and 5,8,11,14,1 7-cis eicosapentaenoic acid (hereinafter called EPA) are preferred as omega-3 polyunsaturated fatty acids.

They are used, in conformity with the invention, as such or in the form of esters, preferably ethylesters, or in the form of inorganic salts, for example with alkaline or alkaline-earth metals, or of organic salts, for example with ethanolamine, choline, and alkanolamines in general, alkylamines or finally with basic amino acids, preferably arginine or lysine.

It is understood that DHA and EPA, in any of the above described forms, can be used individually, or as a mixture of the two. The mixtures are prepared by combining the desired quantities of the purified constituents; alternatively the DHA and EPA mixtures or the mixtures of their esters or salts thereof are used, as obtained by extraction, purification and concentration processes of the two acids starting from their natural sources (mainly fish oils).

As regards the reducing vitamins, the vitamins E, A and C are preferably used. The term 'vitamin E' is to be understood as inclusive of α-tocopherol, both in the d- and and dl- form, as well as the other tocopherols (β, α, etc.) in the various stereoisomeric or racemic forms, while the term 'vitamin A' stands for retinal and dihydroretinol. Derivatives of vitamin E and of vitamin A, endowed with vitamin-like action, such as the esters, preferably the acetates, succinates, palmitates, are also conveniently used. In conformity with the invention, the so-called 'provitamins A', that is, the carotenes, preferably β- and α-carotene can also be associated with DHA and EPA. Vitamin C is also conveniently used in combination with EPA and DHA. Owing to its fat-insolubility, this vitamin is used in the form of an ester, specially the palmitate. Alternatively it is used as a sodium salt together with EPA and DHA salts, in aqueous liquid formulations. The reducing vitamins or provitamins are combined with DHA and EPA in substantial quantities, 10% to 40% by weight, preferably 20% to 30%.

Long chain polyunsaturated fatty acids, in particular those of the omega-3 series, of which DHA and EPA are the most interesting, have recently stimulated great interest as agents useful in the prevention and treatment of numerous pathological forms, specially those related to the cardiocirculatory system. The literature has described DHA and EPA effects against platelet aggregation, as well as their anti-atheromatous and antithrombotic action (cif. for instance A. Leaf and P. C. Weber, New England J. Med., 318, 549, 1988) and their antihypertriglyceridemic and antihypercholesterolemic actions. Additional possible instances of DHA and EPA application are the inflammatory pathologies (cif. S. P. Prescott, J. Biol. Chem., 259, 7615, 1984), some neoplastic forms (cif. H. O. Bang et al., Acta Med. Scand., 220, 69, 1976), psoriasis, memory and learning disturbances, some central nervous and peripheral pathologies, etc.

Specially interesting is the antiatherogenous action of EPA and DHA, above all in view of atherosclerosis wide diffusion in the affluent society, in relation also to the alimentary habits and life style. Though thorough studies are still ongoing, it is already possible to advance hypotheses on the mechanism through which this action takes place. The omega-3 fatty acids, by replacing arachidonic acid as cyclo-oxygenase substrates, are oxidised to thromboxane A3 (not so active as platelet pro-aggregant and vasoconstrictor as thromboxane A2, an arachidonic acid metabolite) and to prostaglandin PGI3, having, by converse, anti-aggregant and vasodilator properties similar to those of prostaglandin PGI2, produced through oxidation of arachidonic acid. The final overall result is a more powerful inhibition of platelet aggregation and an increased vasodilation, that is, a more favourable interaction between platelets and vasal wall.

On the other hand, however, experimental tests in vitro and in vivo have drawn the attention to a possible cause of troubles in the dietetic or therapeutic use of DHA and EPA or of their derivatives. Their administration, in addition to the other effects, leads to their incorporation into the lipoproteins which, precisely for the increased presence of highly unsaturated acids, become more susceptible to oxidative changes. It is known that oxidation of low-density proteins (LDL) is one of the first stages in the atherogenesis process, stimulating the vascular wall cells to produce cytokines, a cause of local inflammatory reaction (cif. for instance De Maat, Princen, Thromb. Haemost., 69, 6, 1069, 1993). The onset of thrombosis and atherosclerosis is favoured, manifestations which are, paradoxically, two pathologic conditions against which DHA and EPA have shown, in other respects, a marked therapeutic potential.

It has now been found that administration of DHA and EPA, as such or in the form of esters or of salts, in combination with suitable quantities of vitamin E, as previously defined, substantially inhibits the oxidative processes in vivo of the two polyunsaturated acids and for this reason counteracts the oxidation processes, specially those involving LDL, which in the end, favour the onset of atherosclerosis.

Next to the specific action against oxidation of DHA and EPA incorporated in the LDLs, vitamin E carries out an effective action in vivo also against other oxidation and peroxidation processes involved in the genesis of atherosclerosis, e.g., through effective prevention of free-radical (superoxide anion, singlet oxygen, etc.) and hydrogen peroxide formation, now known to favour the onset of atherosclerotic, ischemic and neoplastic diseases.

Also vitamin A and provitamins A (carotenes), as well as vitamin C (ascorbic acid), present in blood, even though in much smaller quantity than that of α-tocopherol, perform an antioxidative action against LDLs, contributing to inhibit atherogenetic processes. The foregoing information defines the advantage of DHA and EPA use in combination with reducing vitamins or provitamins in the treatment and in the prevention of atherosclerosis, as well as in other pathologic conditions of the cardiovascular system connected with atherosclerosis.

In the course of our work on LDL oxidizability we have surprisingly found that the effect on LDL oxidation by EPA and DHA in combination with reducing vitamins and provitamins is not simply additive but produces a true synergistic effect. In a typical experiment, different groups of rats were treated for 6 weeks as follows:

Group 1: 8 mg/kg of vitamin E (dl-α-tocopherol)
Group 2: 25 mg/kg of DHA
Group 3: 8 mg/kg of vitamin E+25 mg/kg of DHA (in the ratio of about 30:100)
Group 4: 25 mg/kg of an EPA+DHA ethyl ester mixture (total ethyl esters 85%; EPA/DHA ratio 1/1
Group 5: 8 mg/kg of vitamin E+25 mg/kg of the above mentioned mixture of EPA+DHA ethyl esters (in the ratio of about 30:100)
Group 6: 20 mg/kg of vitamin E+25 mg/kg of the above mentioned mixture of EPA+DHA ethyl esters (in the ratio of about 80:100)
Group 7: 1.25 mg/kg of vitamin E+25 mg/kg of the above mentioned mixture of EPA+DHA ethyl esters (in the ratio of about 5:100)

At the end of treatment the blood LDL fraction was isolated and Oxidised with 5M $Cu^{2+}$ at 37° C. for 8 h, the oxidation progress being controlled at the following times: 0, 1, 3, 5, 8 h (cif. Jialal, Vega et al., Atherosclerosis, 84, 185, 1990). To measure oxidation the Thiobarbituric Acid-Reacting Substances (TBARS) test, expressed as malondialdehyde (MDA) equivalent, was used, according to a known method (cif. Jialal, Freeman et al., Arterioscl. Thromb., 11, 482, 1991). The following table I reports the test results.

TABLE 1

| LDL oxidation speed, expressed as nanomols of MDA/mg of proteins/hour, after 6 weeks of treatment per os in rats. | |
| --- | --- |
| Control group | 23.1 |
| Group 1 (vitamin E) | 15.5 |
| Group 2 (DHA) | 27.3 |
| Group 3 (vit. E 30% with DHA) | 9.8 |
| Group 4 (EPA + DHA ethylesters) | 27.7 |
| Group 5 (vit. E 30% with EPA + DHA esters) | 9.3 |
| Group 6 (vit. E 80% with EPA + DHA esters) | 10.1 |
| Group 7 (vit. E 5% with EPA + DHA esters) | 21.9 |

From the above results EPA and DHA, individually (DHA) or in a mixture (EPA+DHA esters), are shown to increase LDL oxidation to a not negligible extent, while the combined use of EPA/DHA plus a quantity equivalent to the 30% of their weight of vitamin E considerably decreases oxidation, to an extent higher than vitamin E alone. The use of a quantity equivalent to 80% of vitamin E together with EPA+DHA ethylesters (group 6) affords no special advantage as compared to the 30% while a limited quantity, in the order of 5% (group 7) has practically no effect.

With reference to the literature on the subject, it is worth mentioning that only German Patent no. 3.719.097 claims the use of EPA and DHA in combination with high quantities of vitamin E, for normalisation of blood coagulation (which undergoes alteration during treatment with EPA and DHA alone), differently from the present patent application.

Said German Patent particularly claims a drug containing EPA and DHA as well as vitamin E, characterized in that the content in vitamin E is 40–100% by weight in respect of the fatty acids and states that smaller quantities have no therapeutic action (they cannot normalise prothrombin time): on the contrary, we have found that, in order to counteract oxidation of the LDLs (and therefore—among others—the onset of atherosclerosis), much smaller quantities of vitamin are already sufficient to obtain maximum efficacy, ranging such quantities from 10 to 40% of the weight of the fatty acids, and preferably from 20 to 30%. Higher quantities have no additional activity and are not considered useful, and might even prove toxic considering the high doses of polyunsaturated acids advocated for clinical use.

Other Authors report the possibility of adding vitamin E (or other antioxidants) for the preservation of polyunsaturated fatty acids in vitro. In all these cases however the quantity normally used as an antioxidant in vitro is quite small and does not exceed a small percentage by weight in respect to the active substance (1–2% maximum). If at all, British Patent no. 2.218.904 briefly mentions the therapeutic use of DHA ethyl ester combined with 5–10% of α-tocopherol and claims the relative formulation. At these concentrations, however, we have shown that tocopherol effect on in vivo peroxidation of the omega-3 acids incorporated in the LDLs is practically negligible (cif. Table 1-group 7).

On the contrary, the pharmaceutical formulations, subject of the present invention are characterized by substantial quantities of reducing vitamins or provitamins which protect DHA and EPA from oxidation in vivo by interacting with the metabolic processes, that is, just as already reported, in the ratio of 10–40% in respect to the polyunsaturated acids, preferably from 20% to 30%.

All in all, it can be concluded that the use of EPA/DHA or of their salts and derivatives in combination with reducing vitamins or provitamins optimize the therapeutic activity of omega-3 polyunsaturated acids, meanwhile inhibiting oxidation of said acids, which is a possible cause of serious side effects such as the onset of atherosclerosis.

Moreover, as already mentioned, the concomitant use of highly fat-soluble substances such as EPA and DHA, and of vitamins E, A, C and carotenes, enhances their reciprocal absorption capacity and their bioavailability following administration by oral route.

Also as regards other types of pathology against which DHA and EPA are used (such as inflammation, psoriasis, neoplastic forms, memory and learning disturbances, central and peripheral nervous system diseases), the concomitant presence of reducing vitamins or provitamins having in vivo a protection effect on DHA and EPA is anyhow beneficial.

This effect is quite different and more complex than the already mentioned simple antioxidative effect in vitro which the tocopherols, the carotenes and vitamin A and C could have on the oxidizable substances.

The optimal quantity of DHA and EPA acids, their esters or salts, together with the established quantity of reducing vitamin or provitamin may be distributed into soft gelatin capsules, using conventional techniques, solvents and diluents, such as triacetin, polyethyleneglycol mixtures (PEG 200–600+PEG 4000), and tweens optionally in a mixture with small quantities of ethanol, propylene glycol etc. As an alternative, the acids and the reducing vitamins and provitamins are adsorbed on highly porous material (for example suitably treated silica or alumina) or on materials with which they form true inclusion complexes (e.g., zeolites and cyclodextrins), obtaining solid powders which can be formulated e.g., in the form of tablets, coated tablets etc. If EPA and DHA are used in the form of salts and antioxidant water-soluble vitamins, e.g., vitamin C (ascorbic acid), in the form of sodium salt, the compositions may be in liquid form (drops, syrups, single-dose drinkable vials etc.). Finally, by using suitable excipients and adjuvants, topical dosage forms such as creams may be obtained.

The following examples further illustrate the invention.

Formulation as soft gelatin capsules

EXAMPLE NO. 1

| | |
|---|---|
| DHA ethylester (325.6 mg), equivalent to DHA | 300 mg |
| dl-α-tocopherol | 90 mg |
| Triacetin | 100 mg |
| Gelatin | 127 mg |
| Ethyl and propyl p-hydroxybenzoate sodium, respect. | 0.58 and 0.29 mg |

EXAMPLE NO. 2

| | |
|---|---|
| DHA ethanolamine salt (339.4 mg), equivalent to DHA | 300 mg |
| dl-(α- tocopherol acetate | 65 mg |
| Triacetin, gelatin, ethyl and propyl p-hydroxybenzoate sodium: | as in Example no. 1 |

EXAMPLE NO. 3

| | |
|---|---|
| EPA salt of arginine (454.9 mg) equivalent to EPA | 300 mg |
| Retinol acetate | 70 mg |
| Triacetin, gelatin, ethyl and propyl p-hydroxybenzoate sodium: | as in Example no. 1 |

EXAMPLE NO. 4

| | |
|---|---|
| DHA ethylester (162.8 mg) equivalent to DHA | 150 mg |
| EPA ethylester (163.9 mg) equivalent to EPA | 150 mg |
| dl-α-tocopherol | 60 mg |
| Triacetin, gelatin, ethyl and propyl p-hydroxybenzoate sodium: | as in Example no. 1 |

EXAMPLE NO. 5

| | |
|---|---|
| EPA | 1000 mg |
| Ascorbyl palmitate | 250 mg |
| Triacetin | 160 mg |
| Gelatin | 220 mg |
| Ethyl and propyl p-hydroxybenzoate sodium | 1.9 and 0.97 mg |

EXAMPLE NO. 6

| | |
|---|---|
| DHA | 300 mg |
| dl-α-tocopherol | 59 mg |
| Ventilated silica | 600 mg |
| Magnesium stearate | 15 mg |
| Gelatin | 125 mg |
| Ethyl and propyl p-hydroxybenzoate sodium | 0.58 and 0.29 mg |

I claim:

1. A pharmaceutical composition, comprising from 10–40% by weight Vitamin E, and a remainder by weight of a combination of (a) 4,7,10,13,16,19-cis docosahexaenoic acid (DHA),esters or salts thereof and (b) 5,8,11,14,17-cis eicosapentaenoic acid (EPA), pharmaceutically acceptable esters, or salts thereof.

2. A pharmaceutical composition according to claim 1, comprising between 20–30% vitamin E.

3. A pharmaceutical composition according to claim 1, comprising ethyl esters of DHA and EPA.

4. A pharmaceutical composition according to claim 1, comprising ethyl esters of DHA and EPA.

5. A pharmaceutical composition according to claim 1, comprising between 50 to 1,000 mg of DHA and EPA.

6. A pharmaceutical composition according to claim 2, comprising between 50 to 1,000 mg of DHA and EPA.

7. A pharmaceutical composition according to claim 3, comprising between 50 to 1,000 mg of DHA and EPA.

\* \* \* \* \*